United States Patent [19]

Saltzman

[11] 4,380,586
[45] Apr. 19, 1983

[54] METHOD AND APPARATUS FOR PHOTOMETRICALLY MONITORING LOW LEVEL CONCENTRATION OF HYDROGEN SULFIDE IN ALKANOL AMINE

[75] Inventor: Robert S. Saltzman, Wilmington, Del.

[73] Assignee: E. I. Du Pont de Nemours and Company, Wilmington, Del.

[21] Appl. No.: 310,451

[22] Filed: Oct. 13, 1981

Related U.S. Application Data

[63] Continuation-in-part of Ser. No. 211,582, Dec. 1, 1980, abandoned.

[51] Int. Cl.³ .......................................... G01N 21/75
[52] U.S. Cl. ...................................... 436/121; 422/68
[58] Field of Search ............ 23/232 R, 230 R, 232 E; 422/68, 88, 91, 83; 436/121

[56] References Cited

U.S. PATENT DOCUMENTS 2,554,414  5/1951  McClendon ..................... 422/91
3,338,664  8/1967  Bally et al. ..................... 23/232 R
3,617,136  11/1971  Lyshkow ......................... 422/91 X
3,712,792  1/1973  Lyshkow ......................... 422/91 X Primary Examiner—Arnold Turk

[57] ABSTRACT

A method and an apparatus for photometrically analyzing the hydrogen sulfide concentration in a stream containing at least a first predetermined concentration of bonded hydrogen sulfide-amines and ultraviolet radiation-absorbing impurities is characterized by isolating a first, reference, sample of the stream and removing the hydrogen sulfide from the reference sample until a second, lower, predetermined concentration remains. Thereafter, the first, reference, sample is photometrically analyzed and a reference signal representative of the ultraviolet radiation-absorbing characteristics of the first, reference, sample is produced. The reference signal is thereafter used in the photometric analysis of a second sample to produce a signal representative only of the hydrogen sulfide concentration in the second sample.

26 Claims, 4 Drawing Figures

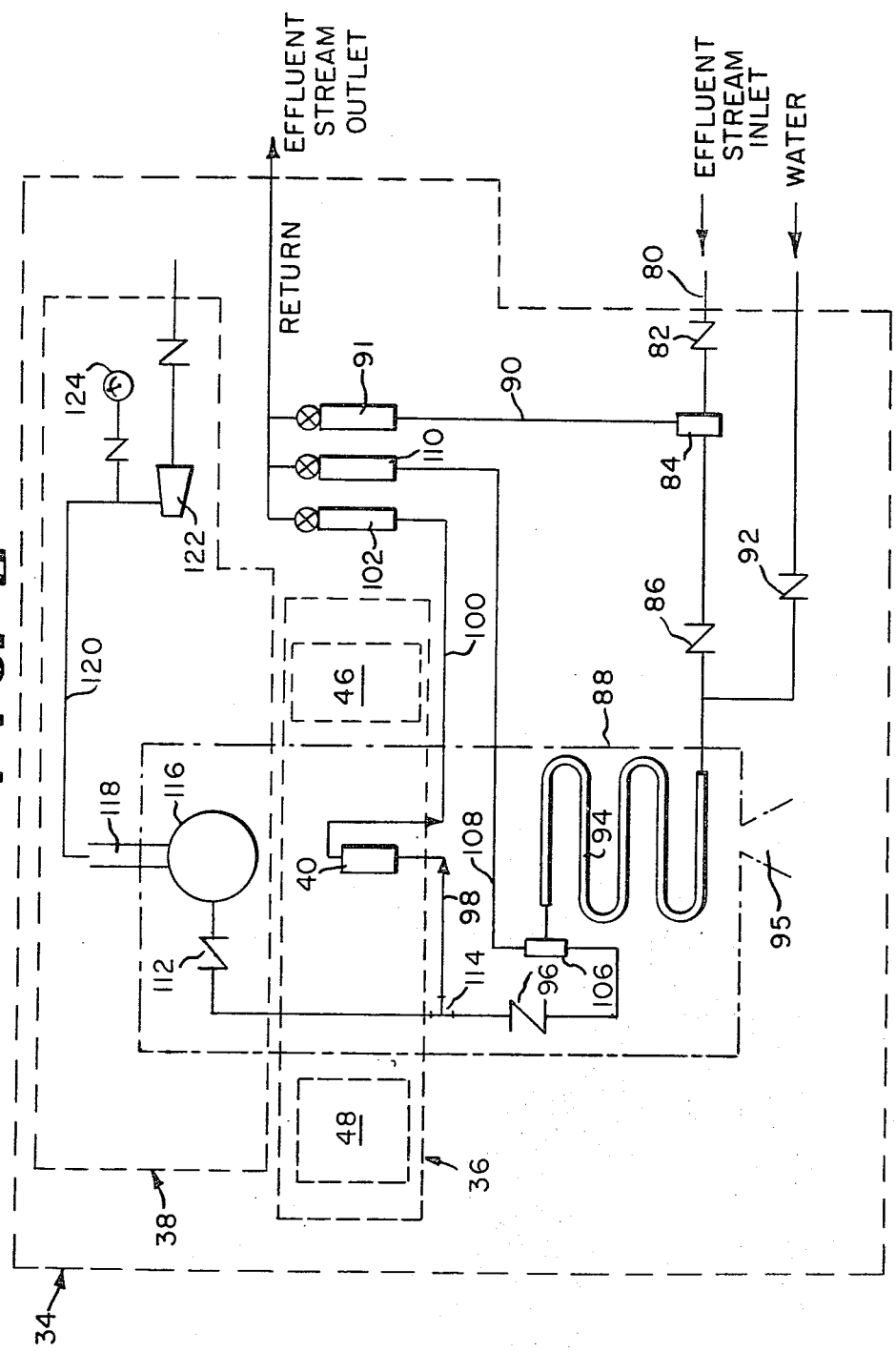

METHOD AND APPARATUS FOR PHOTOMETRICALLY MONITORING LOW LEVEL CONCENTRATION OF HYDROGEN SULFIDE IN ALKANOL AMINE

This application is a continuation-in-part of copending application Ser. No. 211,582, filed Dec. 1, 1980, now abandoned.

BACKGROUND OF THE INVENTION

1. Field of the Invention

This invention relates to photometric analysis of hydrogen sulfide in alkanol amines and, in particular, to a method and apparatus adapted to measure and to compensate for background photometric absorption caused, for example, by impurities in the amine stream so that an accurate measurement of the concentration of hydrogen sulfide may be obtained.

2. Description of the Prior Art

The amine absorption process by which hydrogen sulfide is removed from refinery "sour" gas is well-known. The mechanism by which hydrogen sulfide is eliminated is understood and relates to the bonding of hydrogen sulfide with an alkanol amine. Typically, a "lean" amine, that is, an amine having an available site at which to bond with hydrogen sulfide, is introduced near the top of a countercurrent absorption tower, or absorber, while a sour gas stream is introduced near the bottom of the absorber. A chemical reaction within the absorber occurs wherein the hydrogen sulfide is bonded to the alkanol amine. The resultant bonded amine, or so-called "rich" amine, is then pumped to the inlet of a stripping column wherein the high temperature associated with high pressure steam is used to strip the hydrogen sulfide from the bonded amines. The stripped amines are conveyed, after cooling, to the absorption tower and the cycle is completed.

The amine-absorption desulfurization process is described in a paper written by R. S. Saltzman entitled "Continuous Photometric Analysis for Measurement and Control in Sulfur Recovery Operations" presented at the Texas A&M University Instrumentation Symposium for Process Industries, January 1977.

For various economic reasons the amount and cost of energy utilized to produce high pressure steam used in the stripping column has become the focus of conservation activity. When energy costs and availability were less important considerations it was the typical practice to use steam to lower the concentration of hydrogen sulfide to a level below that necessary for efficient absorption in the absorber. However, as the cost of energy has increased, this practice is no longer economical. It is, accordingly, important to provide some indication as to the level of hydrogen sulfide remaining in the effluent from the stripping column so that the efficiency of the stripping column may be optimized from an energy consumption standpoint.

To this end it is known that photometric analyzers have been utilized to provide an indication of the amount of hydrogen sulfide remaining in the effluent of the stripping column. One such apparatus is described in the above-mentioned article and is sold by E. I. du Pont de Nemours and Company as the 400 Photometric Analyzer. Such apparatus relies upon the strong ultraviolet radiation absorption characteristic of the alkanol amine-hydrogen sulfide bond to measure the hydrogen sulfide concentration in the stripping column effluent. In general, two problems have been observed with regard to obtaining accurate measurements of the hydrogen sulfide concentration.

The first problem relates to the acute temperature sensitivity of the absorption characteristic of the amine-hydrogen sulfide bond. At higher temperatures, more ultraviolet radiation absorption occurs. Accordingly, it has been necessary to provide a stabilizing heat exchanger in the monitoring path upstream of the photometric analyzer to insure that the sample of the effluent from the stripping column introduced into the sample cell of the analyzer is maintained at a predetermined constant temperature. By this expedient it has been found that the effect of temperature on the ultraviolet radiation absorption characteristic of the amine-hydrogen sulfide bond is minimized.

A further problem relates to the effects of recycled impurities in the amine loop. As the amines become recycled repeatedly it is possible that dirt, corrosion inhibitors, or other contaminants produced by chemical breakdown may occur to form such impurities. Such impurities behave as absorbers of ultraviolet radiation at the same wavelengths as are absorbed by an amine-hydrogen sulfide bond. Accordingly, incorrect measurements of the concentration of hydrogen sulfide in the effluent from the stripping column can occur. This could result in the unnecessary increase in steam use with a concomitant increase in energy consumption. Increased energy consumption under these circumstances would not be economically justified and would, therefore, be disadvantageous. It should be noted that the application of the device mentioned in the referenced article was on specially controlled processes where impurities in the stream were maintained at low levels and the sample temperature was closely regulated.

To obtain a measurement of the hydrogen sulfide concentration in a stream it is known also to introduce a sample of the stream that contains bonded hydrogen sulfide-amine into a vessel and to thereafter introduce a predetermined amount of hydrogen chloride into the vessel. The hydrogen chloride replaces the hydrogen sulfide and the hydrogen sulfide is measured to provide an indication of the concentration of hydrogen sulfide in the sample.

SUMMARY OF THE INVENTION

In order to provide an accurate measurement of the hydrogen sulfide concentration in a stream it is essential and advantageous to provide an apparatus and a method for obtaining a reference or baseline to compensate for the changing background absorption caused by concentrations of various impurities in the recycled amines.

The instant invention relates to a method and an apparatus for photometrically analyzing a stream containing bonded hydrogen sulfide-amines and ultraviolet radiation-absorbing impurities in which a reference or baseline level signal representative of the absorption characteristic of ultraviolet radiation of the impurities is generated and applied to "zero out" or otherwise eliminate shifts in the output of the photoanalysis cell so that the concentration of hydrogen sulfide in the stream may be measured.

In accordance with the instant invention a first, or reference, sample of the stream, as the effluent from a stripping column, containing at least a first predetermined concentration of bonded hydrogen sulfide-amines and ultraviolet radiation-absorbing impurities is introduced into a vessel having a predetermined volume. In that vessel substantially all of the hydrogen sulfide in the first sample is removed so that the concentration of hydrogen sulfide is reduced to a second concentration lower than the first concentration. The hydrogen sulfide is removed by the application of predetermined temperature and pressure conditions to the reference sample for a predetermined time period. Thereafter, the first, reference, sample is subjected to photometric analysis and the absorptive characteristic of the first sample provides a signal representative of the ultraviolet radiation-absorbing characteristic of any impurities and remaining hydrogen sulfide therein. This signal provides a reference against which a photometric analysis of a second sample of the effluent of the stripping column may be made. The difference between a signal representative of the ultraviolet radiation-absorbing characteristic of the second sample and the reference signal is functionally related to the concentration of hydrogen sulfide in the second sample.

In accordance with a second embodiment of the invention all of the hydrogen sulfide is removed from the first, reference, sample by displacement using hydrogen chloride. After the first sample is isolated in the vessel hydrogen chloride is introduced thereinto. The hydrogen chloride displaces the hydrogen sulfide to reduce the concentration of hydrogen sulfide in the first sample to zero. The first sample is thereafter photometrically analyzed to obtain a reference signal representative of the ultraviolet radiation absorption characteristic of the impurities remaining therein. This reference signal is taken into account when generating a signal representative of the hydrogen sulfide concentration in a subsequently analyzed second sample.

BRIEF DESCRIPTION OF THE DRAWINGS

The invention will be more fully understood from the following detailed description thereof taken in connection with the accompanying drawings, which form a part of this application and in which:

FIG. 2 is a schematic diagram of an apparatus for providing a reference signal representative of the ultraviolet radiation-absorbing characteristic of impurities (and remaining hydrogen sulfide, if any) in a first sample in accordance with the instant invention;

DETAILED DESCRIPTION OF THE INVENTION

Figure 1:
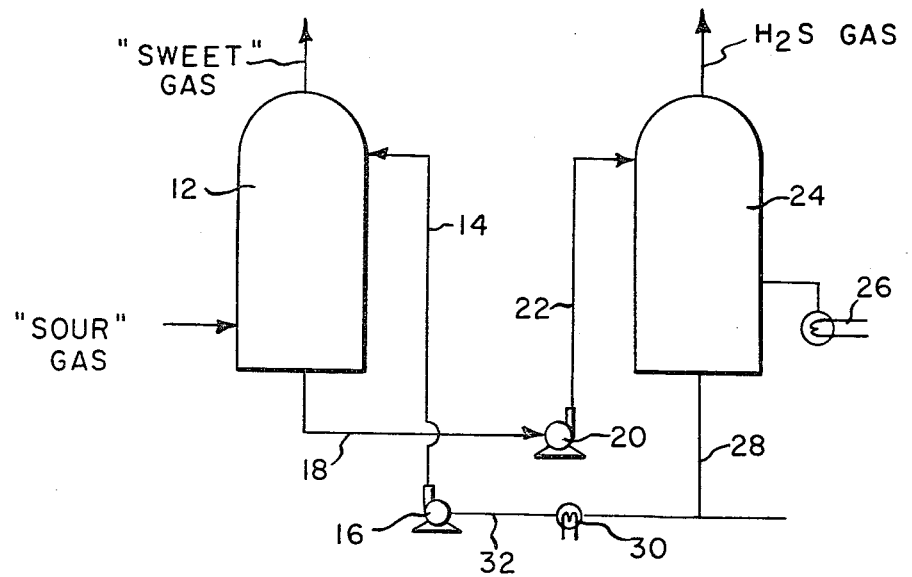
FIG. 1 is a schematic diagram of a typical amine absorption process illustrating an environment in which the invention may be used.

Throughout the following detailed description similar reference numerals refer to similar elements in all figures of the drawings.

With reference to FIG. 1, shown is a schematic diagram of a typical amine absorption process, one of the most common processes for removing hydrogen sulfide contained in the so-called "sour" gas produced in natural gas purification plants, refineries, chemical plants and other industrial processes. The sour gas is conveyed to the inlet of a countercurrent absorption tower 12 in which hydrogen sulfide is removed through absorption by monoethanolamine (MEA), diethanolamine (DEA), or combinations of these two or other alkanol amines. At the outlet of the absorption tower 12 the gas from which the hydrogen sulfide has been removed, the so-called "sweet" gas, is conveyed to storage for further use. Chemically, the hydrogen sulfide and other acid gases (for example, carbon dioxide) attach to amine groups although the binding forces are weak. Other gases in the stream are essentially insoluble in the amine-water solution and are purged through the absorption tower 12.

As shown in FIG. 1, the countercurrent absorption tower 12 receives a charge of "lean" or recycled, stripped amine and water solution through a conduit or pipeline 14 from a pump 16. The chemical bonding which occurs in the absorption tower 12 results in a solution which contains "rich" or bonded hydrogen sulfide-amine. This solution is withdrawn from the lower portion of the tower 12 through a pipeline 18 and is pumped by a pump 20 through a pipeline 22 to the inlet of a stripping column 24. In the stripping column 24 the alkanol amine is heated by steam provided from a source of high temperature, high pressure steam shown schematically at 26. By the action of the heat the hydrogen sulfide is removed (stripped) from the amine. The hydrogen sulfide gas is withdrawn from the outlet at the top of the column 24 and is conveyed to any suitable sulfur recovery unit, such as one operating in accordance with the classic Claus reaction. The effluent solution of water and recycled or stripped amines is conducted from the stripping column 24 through an effluent pipeline 28 where makeup amine from amine storage reservoir may be added. The recycled amine solution is thereafter cooled by a cooler 30 and applied through a pipeline 32 to the recycling pump 16 for reintroduction into the absorption column thus completing the amine loop.

The effluent from the column 24 contains at least a first predetermined concentration of hydrogen sulfide bonded to amines in the amine-water effluent solution. Typically, this first predetermined concentration of hydrogen sulfide lies in the range from about 1200 to 1800 parts per million by weight. As briefly discussed above, in order to control the consumption of energy utilized to generate the steam introduced into the stripping column 28 it is important to monitor the effluent or stripped amine solution at a point downstream of the stripping column 24. Suitable monitoring stations may be located in the outlet pipeline 28, the coolant discharge pipeline 32, and the absorption tower inlet pipeline 14. At whatever location chosen, it is important to monitor for effluent of the stripping column 24 to verify that the column 24 is effectively and economically removing the hydrogen sulfide from the rich amine solution to a concentration which may be efficiently utilized by the absorber 12. This monitoring may be difficult since some alkanol amines (without hydrogen sulfide attached) have background ultraviolet radiation-absorption characteristics. Moreover, repeated cyclings of the amine solution through the amine loop result in the buildup of ultraviolet radiation-absorbing impurities therein. These impurities may include dirt, corrosion inhibitors, or other contaminants produced by chemical breakdown or by corrosion. Whatever their origin, the impurities may also produce some incidental background ultraviolet radiation absorption which, if uncompensated, would lead to erroneous analysis of the effluent of the column 24.

Provided in accordance with this invention is an apparatus and method for compensating for the absorbing characteristics of any impurities and amines which would tend to render the photometric analysis of the effluent from the column 24 inaccurate. As seen in FIG. 2 a photometric analyzing instrument generally indicated by the reference character 34 embodying the teachings of the invention includes a photometric analysis device 36 (shown in more detail in FIG. 3) adapted to measure the concentration of hydrogen sulfide in the effluent derived from a predetermined location in the amine loop. Associated with the analysis device 36 is means 38 for removing hydrogen sulfide from a sample of the effluent to a second concentration lower than the predetermined first concentration prior to the introduction of that sample into the analysis device 36. By removing the hydrogen sulfide in a sample until a second concentration lower than the first predetermined concentration present in the effluent from the column 24 is reached and thereafter photometrically analyzing the sample, an indication of the ultraviolet radiation-absorbing characteristics of the impurities and remaining hydrogen sulfide (if any) may be derived. This indication is useful in serving as a baseline or reference to correct for the effects of ultraviolet radiation absorption caused by such impurities and remaining hydrogen sulfide (if any) when a second sample is analyzed to determine the hydrogen sulfide content therein.

Figure 3:
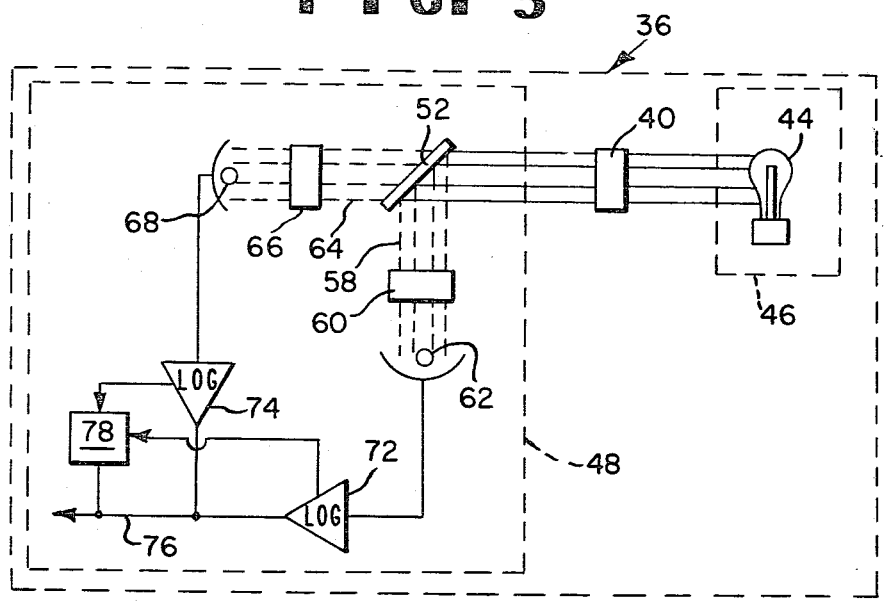
FIG. 3 is a more detailed schematic diagram of a photometric analysis device used in the apparatus of FIG. 2.

As seen in FIG. 3, the analysis device 36 used in connection with the instant invention includes a sample cell 40 and a source of ultraviolet radiation, as a radiation lamp 44, mounted in a source housing 46. Opposite the source housing 46 is a photometer housing 48 which contains a semi-transparent mirror 52. The mirror 52 acts as a beam splitting element to direct a portion of the ultraviolet radiation that has passed through the sample cell 40 along a first optical path 58 containing a first optical filter 60 and a first measuring channel phototube 62. The beam splitter 52 directs the remaining portion of the ultraviolet radiation that has passed through the cell 40 along a second optical path 64 containing a second optical filter 66 and a second reference channel phototube 68. The filters 60 and 66 are provided to pass only radiation having a selected spectral component. The radiation incident on the phototubes 62 and 68 controls the flow of current generated thereby. The greater the concentration of absorbing material within the liquid sample passed through the sample cell 40 the greater is the absorption of ultraviolet radiation at selected wavelengths. Consequently, the current generated by the phototubes is concomitantly reduced. The signals produced by the respective phototubes 62 and 68 represent the absorption characteristics of the sample in the cell 40 at the selected wavelengths of ultraviolet radiation. These signals are related to the concentration of the material in the cell 40 by Beer's law. Thus, in accordance with well-known photometric analysis techniques, suitable electronic components, such as logarithmic amplifiers 72 and 74, may be arranged to generate an electrical signal output on an output line 76 that is functionally related to the concentration of an ultraviolet radiation absorbing material in the cell 40. A full description of the photometric analysis device 36 heretofore described is contained in U.S. Pat. No. 3,306,156 (Glasser), assigned to the assignee of the instant invention. U.S. Pat. No. 3,306,156 is hereby incorporated by reference herein.

A feedback control arrangement 78 is interconnected with the amplifiers 72 and 74 to provide means for zeroing and spanning the signal on the line 76. The feedback control arrangement is also responsive to the signal generated by the amplifier 74 during the period of time that a reference sample of the effluent (produced in a manner discussed herein) is present in the cell 40 to adjust the output signal on the line 76 to a predetermined reference or baseline value corresponding to absorption characteristic of the reference sample of the liquid effluent. As will be seen from the discussion of the embodiment of the invention shown in FIG. 4, all of the hydrogen sulfide in the reference sample is removed, leaving only the effects caused by impurities in the reference sample. The feedback control arrangement 78 appropriately adjusts the signal on the line 76 to a baseline value corresponding to the signal generated by these impurities, thereby eliminating their effect on subsequent analysis. Alternatively, in the embodiment of the invention shown in FIG. 3, the concentration of hydrogen sulfide in the reference sample is reduced to a predetermined concentration lower than the concentration of hydrogen sulfide in the effluent stream. Thus, the signal generated when this reference sample is in the cell 40 shows the effects of both the low concentration of hydrogen sulfide and the impurities. In this instance the feedback control arrangement 78 appropriately adjusts the signal on the line 76 to a baseline value that corresponds only to the portion of the signal produced from the impurities in the reference sample leaving the portion generated by the remaining low concentration of hydrogen sulfide uncompensated. In this way the effects of the impurities are eliminated during subsequent analysis of other samples.

Referring again to FIG. 2, a specimen taken from any predetermined location in the amine loop is introduced into the instrument 34 of the instant invention through an inlet pipeline 80 having an inlet shut off valve 82 disposed therein. The specimen passes through a filter element 84 and is drawn through another shut off valve 86 to a temperature controlled oven 88. The portion of the specimen not drawn toward the temperature controlled oven 88 is conveyed through a return line thence through a flowmeter and valve 91 to a return line leading to the effluent stream outlet. A shut off valve 92 is connected to a water source so that the instrument 34 may be flushed, if desired.

The specimen is introduced into the temperature controlled oven 88 which includes a heat exchanger 94. The temperature controlled oven 88 is provided for the purpose of regulating the temperature of the specimen to a selected temperature such that the variations in absorption generated by the temperature sensitivity of the hydrogen sulfide-amine bond are eliminated. Heated air, introduced through an inlet vent 95, maintains the temperature in the oven 88 constant (to within $\pm 2.0°$ C. of the selected temperature) to bring the temperature of the specimen in the heat exchanger 94 to the selected temperature. The sample cell 40 is itself included within the oven 88. At the outlet of the heat exchanger 94 the heated specimen is conveyed through a sample cell shut off valve 96 and then through a sample cell inlet pipeline 98 to the sample cell 40. A sample cell discharge pipeline 100 at the outlet of the cell 40 is connected through a flowmeter and valve 102 to the return line. A bubble trap 106 may be provided if desired upstream of the sample cell shut off valve 96. The outlet of the bubble trap 106 is conveyed by a pipeline 108 through a flowmeter and valve 110 to the return line.

In accordance with the instant invention the means 38 for removing hydrogen sulfide from a specimen of the effluent includes a sample shut off valve 112 connected at T junction 114 to the sample cell inlet pipeline 98. Connected to the outlet of the sample shut off valve 112 is a vessel 116. The vessel 116 may take any suitable form and is preferably fabricated of corrosion-resistant material. For a purpose made clearer herein the vessel 116 is physically disposed within the temperature controlled oven 88. The outlet of the vessel 116 is connected through a reflux column 118 to an evacuation line 120. The pressure conditions in the vessel are controlled through the evacuation line 120 as operatively controlled by an aspirator 122. A gauge 124 permits the pressure level within the vessel 116 to be monitored and maintained within predetermined limits.

In operation, the analysis instrument 34 is connected at a selected location in the amine loop. As noted the effluent from the column 24 contains a first predetermined concentration of hydrogen sulfide. In order to compensate for the absorptive effects occasioned by the presence of impurities which are present in the amine loop, a first, or reference, sample of the specimen of effluent solution drawn into the instrument 34 is taken by temporarily opening the shut off valve 112. The first, reference, sample of the heated solution is drawn into the vessel 116 under the influence of the vacuum in the line 120. If it is desired to continue analysis of the remainder of the specimen while the effects of impurities are being compensated, the shut off valve 112 is closed while the valve 96 remains open. If it is desired that analysis of the remainder of the specimen be held in abeyance while the effects of impurities are compensated, the valve 96 may also be closed.

In the vessel 116 most of the hydrogen sulfide bonded to the amines within the first, reference, sample within the vessel 116 is removed so that a second concentration of hydrogen sulfide, less than the first predetermined concentration, remains in the reference sample in the vessel. Although the second concentration need only be less than the first concentration, it is preferred that the second concentration of hydrogen sulfide in the reference sample in the vessel 116 be in the range from 400 to 800 parts per million by weight. The concentration of hydrogen sulfide in the vessel 116 is lowered by the application of predetermined temperature and predetermined pressure conditions to the sample in the vessel 116 for a predetermined time period.

It has been found that maintaining the portion of the first reference sample within the vessel 116 for a period of time within the range from thirty to ninety minutes, preferably in the range from fifty to sixty minutes, at a temperature in the range from 60° C. to 80° C. and preferably 70° C. and under a pressure in the range from 1.5 to 2.0 pounds per square inch (absolute) (or "psia"), preferably 2.0 psia results in the removal of the hydrogen sulfide from the reference sample in the vessel 116 to a concentration lower than the first concentration of hydrogen sulfide in the effluent of the column 24. However, if the pressure is in the range from five to seven pounds per square inch (absolute), then the temperature is preferably in the range from 90° C. to 110° C., most preferably 100° C., and the time period is in the range from three to four hours (one hundred eighty to two hundred forty minutes). Operating at the higher temperature makes the measurement less temperature sensitive.

In addition, an air aspirator may be used to achieve the higher absolute pressure. It is preferred that the source of heat applied to the sample in the vessel 116 be derived from the temperature controlled oven 88. However, because of the temperature sensitivity of the measurement, it may be necessary to measure the temperature of the sample cell 40 (by means of a thermistor, for example, to compensate for the change in the alkanol amine-hydrogen sulfide bond absorptivity with a change in temperature to improve the accuracy of the analysis.

At the termination of the hydrogen sulfide removal period the valve 112 is opened and the shut off valve 96 is closed so that the first reference sample is conveyed through the line 98 toward the sample cell 40. In the sample cell 40 the ultraviolet radiation absorptive characteristics of the impurities and remaining hydrogen sulfide in the first reference sample is measured and a signal representative thereof is generated. This signal may be used by the feedback control arrangement to appropriately adjust or "zero" the line 76 to thereby account for the ultraviolet absorption due to any impurities and remaining hydrogen sulfide in the manner discussed above. Thereafter, the valve 112 is closed and a second sample of effluent taken. This second sample is, however, directly routed through the shut off valve 96 and the line 98 to the cell 40 so that the ultraviolet radiation absorption characteristics of the effluent may be measured. However, due to the earlier "zeroing" by the analysis of the first, reference, sample the effect of ultraviolet radiation absorption characteristics by the impurities in the effluent is now taken into account. Thus, the concentration of hydrogen sulfide in the second sample derived in accordance with Beer's Law is more accurately available.

Figure 4:
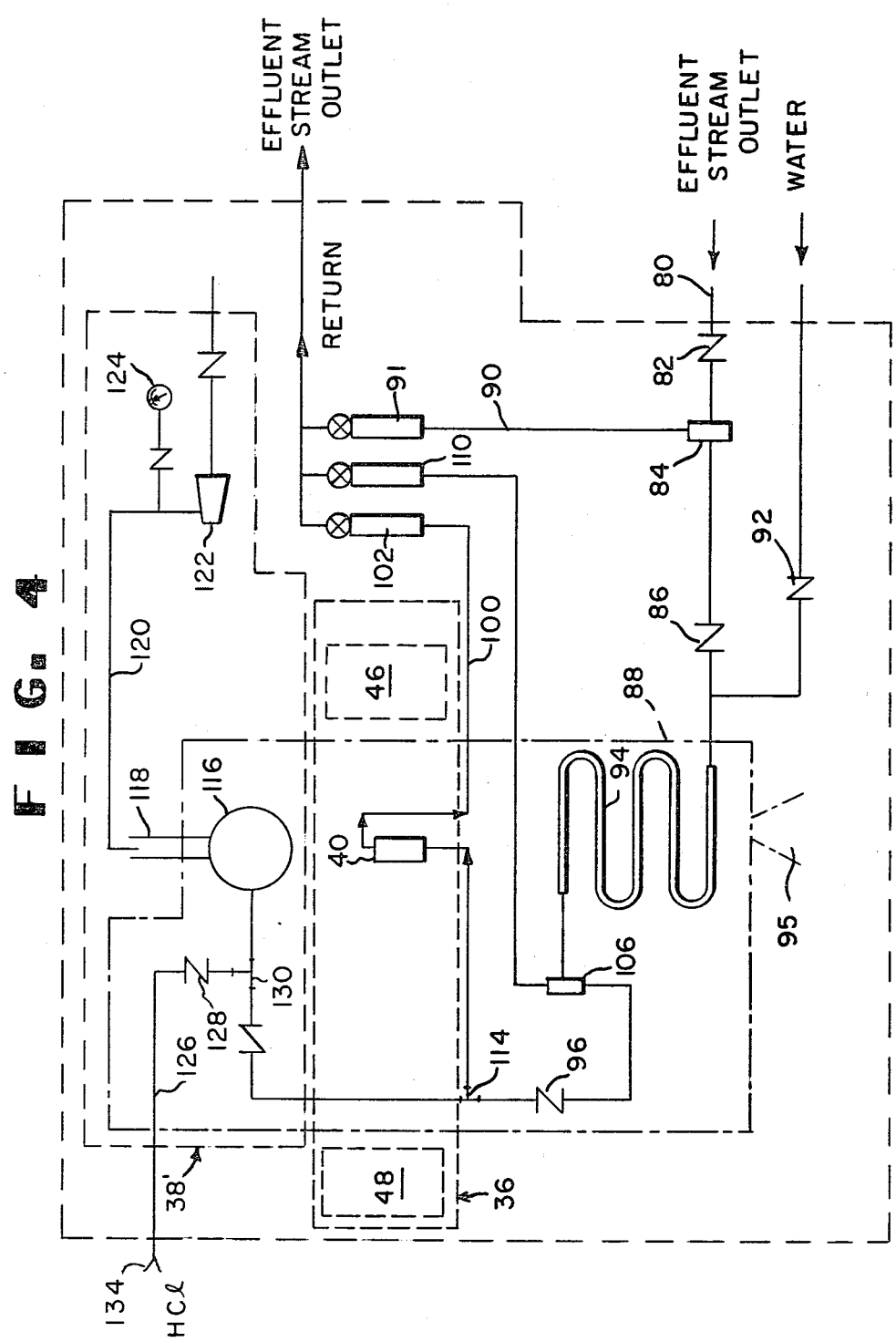
FIG. 4 is a schematic diagram similar to FIG. 2 showing an alternate embodiment of the invention.

With reference to FIG. 4, an alternate embodiment of the hydrogen sulfide removing means 38' in accordance with the instant invention is shown. The embodiment shown in FIG. 4 is identical with that shown in FIG. 2 with the exception that an additional line 126 containing a shut off valve 128 is connected at a T junction 130 upstream of the vessel 116. The line 126 is connected to a source 134 of hydrogen chloride gas.

In accordance with this embodiment of the invention the hydrogen sulfide carried by the effluent amine solution is introduced into the vessel 116 and a predetermined volume of hydrogen chloride gas about twenty percent more than is required to fill all of the amine sites is added thereto. The hydrogen chloride, being a stronger acid, displaces all of the hydrogen sulfide in the amine bond. The hydrogen sulfide is drawn off by the aspirating line 120 leaving in the vessel 116 a reference sample in which the hydrogen sulfide has been removed by displacement with hydrogen chlorine. (In this instance, the second concentration of hydrogen sulfide is zero, since all hydrogen sulfide has been replaced by hydrogen chloride). The amine-hydrogen chloride bond has the same ultraviolet radiation absorption characteristics as unbonded alkanol amine. Thereafter, the first, reference, sample is introduced into the sample cell 40 in a manner similar to that discussed earlier and the background reference of ultraviolet absorption due to impurities is measured and appropriate electronic compensation is made. Thereafter, a signal representative of a second sample is generated. This signal is corrected due to the prior zeroing generated by the analysis of the reference sample and may be used to generate a signal representative of the concentration of hydrogen sulfide in the second sample and, therefore, the effluent stream.

The instrument 34 may be used periodically to manually zero-out the effects of impurities developed in the amine loop. Any convenient periodicity may be chosen (e.g., once per hour) depending upon, for example, changing process conditions. It should be understood, however, that the operation of the instrument 34 in accordance with the invention may be automatically controlled using, for example, a firmware based microprocessor arrangement to automatically control the opening and closing of the various valve elements within the system and to control the application of the appropriate temperature pressure and time parameters used in accordance with the instant invention.

Those skilled in the art, having benefit of the teachings of the instant application, may effect numerous modifications thereto. Those modifications, some of which have been discussed above, are to be construed as lying within the contemplation of the instant invention as defined in the appended claims.

What is claimed is:

1. A method for photometrically analyzing the hydrogen sulfide concentration in a stream containing at least a first predetermined concentration of bonded hydrogen sulfide-amines and ultraviolet radiation-absorbing impurities comprising the sequential steps of:
    (a) removing the hydrogen sulfide from a first, reference, sample of the stream until a second predetermined concentration remains therein;
    (b) photometrically analyzing the first, reference, sample to generate a reference signal representative of the ultraviolet radiation-absorbing characteristics of the remaining hydrogen sulfide and of the impurities in the first, reference, sample; and
    (c) photometrically analyzing a second sample of the stream in a manner which takes into account the reference signal to generate a signal representative of the concentration of hydrogen sulfide therein.

2. The method of claim 1 wherein the removing step (a) comprises the steps of:
    (a1) isolating the first, reference, sample of the stream; and
    (a2) introducing hydrogen chloride into the isolated first, reference, sample until the second predetermined concentration of hydrogen sulfide is zero.

3. The method of claim 1 wherein the removing step (a) comprises the steps of:
    (a1) isolating the first, reference, sample of the stream; and
    (a2) exposing the isolated first, reference, sample to a predetermined pressure less than atmospheric pressure at a predetermined temperature for a predetermined time period to remove the hydrogen sulfide from the first, reference, sample to the second predetermined concentration.

4. The method of claim 3 wherein the predetermined pressure lies within the range from 1.5 to 2.0 pounds per square inch (absolute).

5. The method of claim 3 wherein the predetermined pressure is 2.0 pounds per square inch (absolute).

6. The method of claim 3, 4 or 5 wherein the predetermined temperature lies within the range from 60° C. to 80° C.

7. The method of claim 6 wherein the predetermined temperature is 70° C.

8. The method of claim 7 wherein the predetermined time period lies in the range from thirty to ninety minutes.

9. The method of claim 8 wherein the predetermined time period lies in the range from fifty to sixty minutes.

10. The method of claim 3, 4, or 5 wherein the predetermined time period lies in the range from thirty to ninety minutes.

11. The method of claim 6 wherein the predetermined time period lies in the range from thirty to ninety minutes.

12. The method of claim 11 wherein the predetermined time period lies in the range from fifty to sixty minutes.

13. The method of claim 10 wherein the predetermined time period lies in the range from fifty to sixty minutes.

14. The method of claim 3 wherein the predetermined pressure lies within the range from 5.0 to 7.0 pounds per square inch (absolute).

15. The method of claim 14 wherein the predetermined temperature lies within the range from 90° C. to 110° C.

16. The method of claim 15 wherein the predetermined temperature is 100° C.

17. The method of claim 3, 14 or 16 wherein the predetermined time period lies in the range from three to four hours.

18. The method of claim 15 wherein the predetermined time lies in the range from three to four hours.

19. A method for photometrically analyzing the hydrogen sulfide concentration in a stream containing at least a first predetermined concentration of bonded hydrogen sulfide-amines and ultraviolet radiation-absorbing impurities comprising the sequential steps of:
    (a) isolating a first, reference, sample of the stream;
    (b) removing the hydrogen sulfide from the first, reference, sample to lower the concentration of hydrogen sulfide therein to a second predetermined concentration;
    (c) photometrically analyzing the first, reference, sample to generate a reference signal representative of the ultraviolet radiation-absorbing characteristics of the remaining hydrogen sulfide and of the impurities in the first, reference, sample;
    (d) photometrically analyzing a second sample of the stream to generate a second signal representative of the ultraviolet radiation-absorbing characteristics of the bonded hydrogen sulfide-amines and ultraviolet radiation-absorbing impurities therein; and
    (e) generating a signal functionally related to the second signal and to the reference signal and representative of the concentration of hydrogen sulfide in the second sample.

20. The method of claim 19 wherein the removing step (b) comprises the step of:
    (b1) introducing hydrogen chloride into the isolated, first, reference, sample to reduce the concentration of hydrogen sulfide therein to zero.

21. The method of claim 19 wherein the removing step (b) comprises the step of:
    (b1) maintaining the isolated first, reference, sample at a predetermined pressure less than atmospheric pressure and at a predetermined temperature for a predetermined time period to lower the concentration of hydrogen sulfide to the second predetermined concentration.

22. The method of claim 21 wherein the predetermined pressure lies in the range from 1.5 to 2.0 pounds per square inch (absolute), wherein the predetermined temperature lies in the range from 60° C. to 80° C. and the predetermined time period lies in the range from thirty to ninety minutes.

23. The method of claim 21 wherein the predetermined pressure lies in the range from 5.0 to 7.0 pounds per square inch (absolute), wherein the predetermined temperature lies in the range from 90° C. to 110° C., and the predetermined time period lies in the range from three to four hours.

24. In apparatus for photometrically analyzing the hydrogen sulfide concentration in a stream containing at least a first predetermined concentration of bonded hydrogen sulfide-amines and ultraviolet radiation-absorbing impurities the improvement which comprises:
a vessel for receiving therein a reference sample of the stream;
means for removing hydrogen sulfide from the reference sample until a second predetermined concentration of hydrogen sulfide remains therein; and
a photometric analysis instrument adapted to analyze the reference sample to generate an electrical reference signal representative of the ultraviolet radiation-absorbing characteristics of the remaining hydrogen sulfide and of the impurities in the reference sample and to analyze a second sample of the stream in a manner which takes into account the reference signal to generate a signal representative of the concentration of hydrogen sulfide in the second sample.

25. Apparatus according to claim 24 wherein said removing means comprises:
an aspirating system for drawing the reference sample into the vessel and maintaining the reference sample at a predetermined pressure less than atmospheric pressure for a predetermined time period; and
means for applying heat at a predetermined temperature to the reference sample while it is in the vessel to remove the hydrogen sulfide from the reference sample to the second predetermined concentration.

26. Apparatus according to claim 24 wherein said removing means comprises:
an aspirating system for drawing the reference sample into the vessel; and
a conduit arrangement for introducing a predetermined amount of hydrogen chloride into the vessel to remove the hydrogen sulfide from the reference sample until the second predetermined concentration of hydrogen sulfide is zero.

* * * * *